US012630798B2

(12) United States Patent
Wang

(10) Patent No.: US 12,630,798 B2
(45) Date of Patent: May 19, 2026

(54) CULTURE DEVICES

(71) Applicant: SHANGHAI RUIYU BIOTECH CO., LTD., Shanghai (CN)

(72) Inventor: Xuan Wang, Shanghai (CN)

(73) Assignee: SHANGHAI RUIYU BIOTECH CO., LTD., Shanghai (CN)

( * ) Notice: Subject to any disclaimer, the term of this patent is extended or adjusted under 35 U.S.C. 154(b) by 796 days.

(21) Appl. No.: 17/936,904

(22) Filed: Sep. 30, 2022

(65) Prior Publication Data

US 2023/0113710 A1    Apr. 13, 2023

(30) Foreign Application Priority Data

Oct. 8, 2021    (CN) ........................... 202111170828.8
Oct. 8, 2021    (CN) ........................... 202122420855.8

(51) Int. Cl.
*C12M 1/00*        (2006.01)
*C12M 1/26*        (2006.01)
*C12M 3/00*        (2006.01)

(52) U.S. Cl.
CPC ............ *C12M 29/04* (2013.01); *C12M 23/38* (2013.01); *C12M 23/48* (2013.01); *C12M 33/04* (2013.01); *C12M 33/14* (2013.01)

(58) Field of Classification Search
CPC ............................... C12M 29/04; C12M 23/16
See application file for complete search history.

(56) References Cited

U.S. PATENT DOCUMENTS 4,748,124 A  *  5/1988  Vogler .................... C12M 23/34
                                                      435/297.1
4,940,547 A  *  7/1990  Cho ........................ C12M 47/10
                                                      210/643
4,990,256 A  *  2/1991  Schmidt ............... B01D 63/084
                                                      210/636
5,462,874 A     10/1995  Wolf et al.
6,228,607 B1 *  5/2001  Kersten .................. C12M 23/24
                                                      435/297.5
10,087,422 B2 * 10/2018  Ingber .................... C12M 35/08
              (Continued)

FOREIGN PATENT DOCUMENTS

CN        206385177 U    8/2017
CN        210826140 U    6/2020
              (Continued)

OTHER PUBLICATIONS

The Extended European Search Report in European Application No. 22200447.5 mailed on Feb. 21, 2023, 9 pages.

*Primary Examiner* — Jonathan M Hurst
(74) *Attorney, Agent, or Firm* — METIS IP LLC

(57)        ABSTRACT

One or more embodiments of the present disclosure relate to a culture device, which comprises: an accommodation base, an accommodation chamber disposed on the accommodation base. The accommodation chamber includes a culture chamber for accommodating one or more cultures. The culture chamber includes a chamber bottom wall and a chamber side wall surrounding the chamber bottom wall. A culture solution channel is formed between an outer side of the chamber side wall and an inner wall of the accommodation chamber. At least part of the chamber side wall includes a membrane material, and a plane where the membrane material is located intersect with the chamber bottom wall.

19 Claims, 12 Drawing Sheets

(56)            References Cited

U.S. PATENT DOCUMENTS

| | | | | |
|---|---|---|---|---|
| 2007/0042490 | A1* | 2/2007 | Welter | C12M 21/08 |
| | | | | 435/325 |
| 2008/0194017 | A1* | 8/2008 | Esser | C12M 23/12 |
| | | | | 435/307.1 |
| 2009/0298164 | A1 | 12/2009 | Cattadoris et al. | |
| 2011/0044865 | A1* | 2/2011 | Groisman | C12M 41/36 |
| | | | | 422/503 |
| 2011/0306081 | A1* | 12/2011 | Szita | C12M 23/26 |
| | | | | 435/395 |
| 2012/0135452 | A1* | 5/2012 | Shuler | C12M 29/00 |
| | | | | 435/395 |
| 2013/0005027 | A1 | 1/2013 | Paullier et al. | |
| 2013/0059322 | A1* | 3/2013 | Hung | C12M 25/14 |
| | | | | 435/29 |
| 2013/0143230 | A1* | 6/2013 | Tolias | C12Q 1/025 |
| | | | | 435/7.1 |
| 2018/0031564 | A1* | 2/2018 | Su | C12M 23/16 |
| 2018/0326417 | A1* | 11/2018 | Wikswo | C12M 23/34 |
| 2018/0327702 | A1* | 11/2018 | Gannon | C12M 23/16 |
| 2019/0048305 | A1 | 2/2019 | De et al. | |
| 2020/0123488 | A1* | 4/2020 | McCain | C12M 23/24 |
| 2021/0318226 | A1* | 10/2021 | Handique | C12M 47/04 |
| 2022/0362772 | A1* | 11/2022 | Wang | C12M 23/16 |
| 2023/0381773 | A1* | 11/2023 | Takahashi | C12M 23/16 |

FOREIGN PATENT DOCUMENTS

| | | |
|---|---|---|
| CN | 216663114 U | 6/2022 |
| DE | 202018000370 U1 | 4/2018 |
| EP | 0363262 A1 | 4/1990 |
| EP | 2955220 A1 | 12/2015 |
| FR | 1448148 A | 8/1966 |
| JP | 2011206045 A | 10/2011 |
| WO | 2012118799 A2 | 9/2012 |
| WO | 2015032889 A1 | 3/2015 |
| WO | 2018094003 A1 | 5/2018 |

* cited by examiner

100

133

130

150

160

120

100

114(181)

115

1151

121(140)

111
(181)

120

100

CULTURE DEVICES

CROSS-REFERENCE TO RELATED APPLICATIONS

This application claims priority of Chinese Patent Application No. 202111170828.8, filed on Oct. 8, 2021, and Chinese Patent Application No. 202122420855.8, filed on Oct. 8, 2021, the contents of each of which are incorporated herein by reference in their entirety.

TECHNICAL FIELD

The present disclosure relates to the field of biotechnology, in particular to a culture device.

BACKGROUND

When using a culture device for biological culture, a membrane material may be disposed on a culture chamber of the culture device. A selective filterability of a membrane material enables culture solution to enter and exit the culture chamber through the membrane material, thereby making it convenient for carrying out stationary culture or perfusion culture to a culture. However, the disposing of the membrane material may affect an observation of the culture under a lens by a staff member.

In view of the above problems, it is desirable to provide a culture device that changes a setting position of the membrane material to reduce interference of the membrane material to the staff member in observing the culture under the lens, and improve the culture efficiency and the quality of the final obtained culture at the same time.

SUMMARY

The purpose of the present disclosure is to provide a culture device, which comprises: an accommodation base, wherein an accommodation chamber is disposed on the accommodation base and includes a culture chamber for accommodating a culture. The culture chamber may include a chamber bottom wall and a chamber side wall surrounding the chamber bottom wall. A culture solution channel may be formed between an outer side of the chamber side wall and an inner wall of the accommodation chamber. At least a part of the chamber side wall may include a membrane material, and a plane where the membrane material is located may intersect with the chamber bottom wall.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

Figure 1:
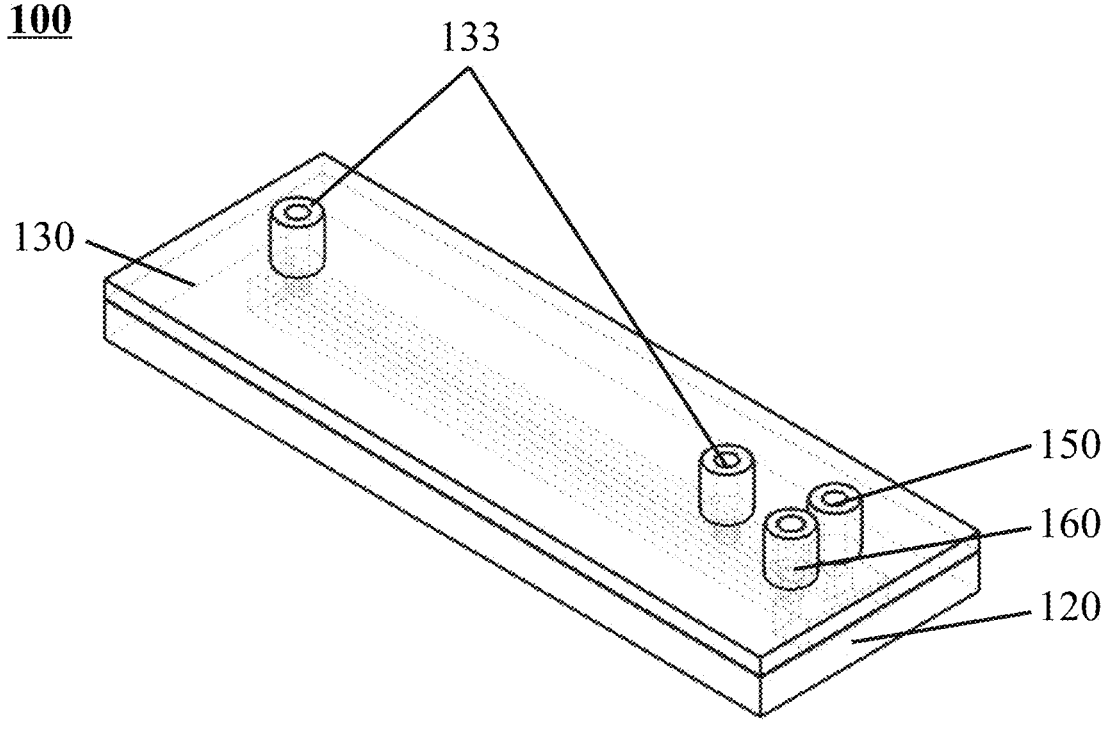
FIG. 1 is a schematic diagram illustrating an exemplary culture device according to some embodiments of the present disclosure.

Labels in the drawings: 100—culture device, 110—culture chamber, 111—chamber side wall, 112—chamber bottom wall, 113—chamber top wall, 114—membrane material, 115—support frame, 1151—support column, 116—chamber bottom plate, 117—chamber side plate, 1131—culture outlet, 1132—culture inlet, 120—accommodation base, 121—accommodation chamber, 130—upper cover, 133—culture inoculation port, 140—culture solution channel, 150—culture solution inlet, 160—culture solution outlet, 170—limiting component, 180—support body, 181—side plate, 182—bottom plate, 183—top plate, 190—locking component.

DETAILED DESCRIPTION

In order to more clearly explain the technical scheme of the embodiment of the present disclosure, the drawings required in the description of the embodiment are briefly introduced below. Obviously, the drawings in the following description are only some examples or embodiments of the present disclosure. For those skilled in the art, the present disclosure can also be applied to other similar situations according to these drawings without paying creative labor. Unless obviously obtained from the context or the context illustrates otherwise, the same numeral in the drawings refers to the same structure or operation.

Those skilled in the art can understand that the terms "first" and "second" in the present disclosure are only used to distinguish different devices, modules, or parameters, and do not represent any specific technical meaning or the necessary logical order between them.

As shown in the present disclosure and claims, unless the context clearly prompts the exception, "a" "one", and/or "the" is not specifically singular, and the plural may be included. In general, the terms "comprises" "comprising" "includes" and/or "including" only indicate that the steps and units that have been clearly identified are included. The steps and units do not constitute an exclusive list, and the method or device may also include other steps or units.

The present disclosure covers any substitution, modification, equivalent method, and scheme defined by the claims on the essence and scope of the present disclosure. Further, in order to make the public have a better understanding of the present disclosure, some specific details are described in detail in the following detailed description of the present disclosure. For those skilled in the art, the present disclosure can be fully understood without the description of these details.

Some embodiments of the present disclosure provide a culture device, which may include a culture chamber and an accommodating component provided with an accommodation chamber. The accommodation chamber may accommodate the culture chamber, and form a culture solution channel with the culture chamber. Through the culture solution channel, culture solution in the culture chamber may be exchanged to realize a stationary culture or a perfusion culture. In a perfusion culture mode, it is necessary to continuously take out a portion of the culture solution and perfuse a new culture solution into the culture solution channel. However, in a stationary culture mode, the culture device is left to stand after the culture solution is perfused into the culture solution channel for the first time, and there is no need to perfuse the new culture solution or take out the part of the culture solution therefrom. In some embodiments, the culture chamber is formed at least by a chamber bottom wall and a chamber side wall surrounding the chamber bottom wall. The chamber side wall may include a membrane material, on which a microporous structure is disposed. On the one hand, the microporous structure may allow the culture solution to flow between the culture chamber and the culture solution channel, on the other hand, the microporous structure may intercept a culture in the culture chamber. In some embodiments, the culture may attach to the chamber bottom wall, grow, and reproduce by obtaining nutrients from the culture solution entering the culture chamber. In some embodiments, when the culture is observed using a microscope, an orientation of the lens (that is, the observation direction) and an illumination direction of a light source are both perpendicular to the chamber bottom wall. Since the membrane material is disposed on the chamber side wall, a surface of the membrane material intersects with the chamber bottom wall. Therefore, a projected area of the membrane material projected on the chamber bottom wall along a direction perpendicular to the chamber bottom wall is smaller, and the projection of the membrane material has less interference to the staff member observing the culture. The intersection between a surface of the membrane material and the chamber bottom wall may mean that the surface of membrane material is inclined relative to the chamber bottom wall, and an angle between the two is within a certain range. In some embodiments, the present disclosure changes the angle between the surface of the membrane material and the chamber bottom wall by disposing the membrane material on the chamber side wall, so as to reduce the interference to the observation of the culture by the staff member. The interference may be caused by the projection of the membrane material on the chamber bottom wall in the direction perpendicular to the chamber bottom wall. At the same time, using the culture device provided by the embodiments of the present disclosure to cultivate may speed up culture efficiency and improve the quality of the obtained culture (for example, the vitality of the culture, a size deviation of the culture, etc.).

Figure 2:
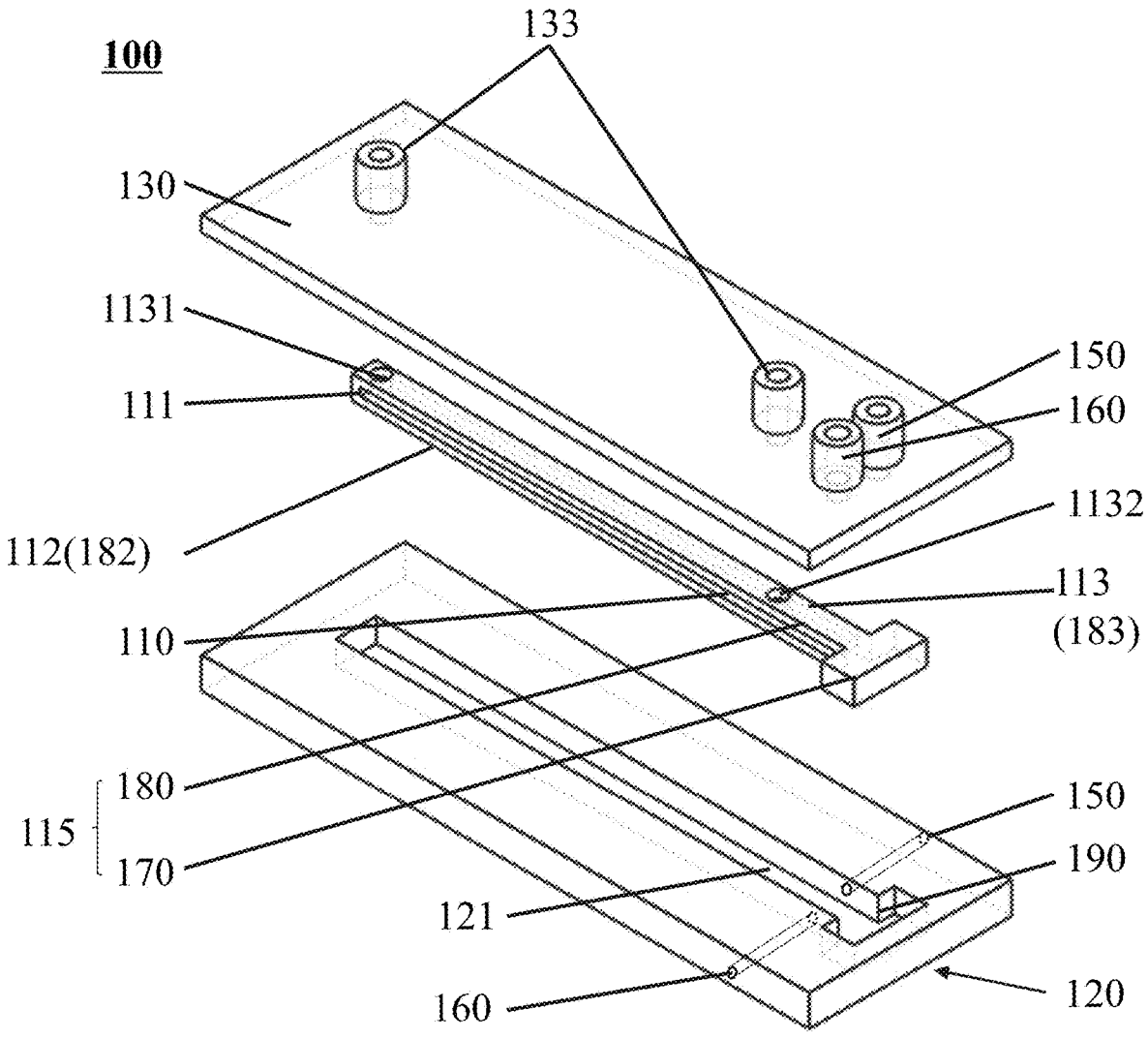
FIG. 2 is a schematic diagram illustrating an explosive view of an exemplary structure of a culture device according to some embodiments of the present disclosure.

FIG. 1 is a schematic diagram illustrating an exemplary culture device according to some embodiments of the present disclosure. FIG. 2 is a schematic diagram illustrating an explosive view of an exemplary structure of a culture device according to some embodiments of the present disclosure. As shown in FIGS. 1 and 2, in some embodiments, a culture device 100 may include a culture chamber 110, an accommodation base 120, an upper cover 130, a culture solution inlet 150, and a culture solution outlet 160. The accommodation base 120 is located at bottom of the culture device 100, the accommodation base 120 may be used to carry and fix the culture chamber 110, and jointly form a culture solution channel 140 with the culture chamber 110. The upper cover 130 may be located on top of the culture device 100. When the culture chamber 110 is placed in an accommodation chamber 121, the upper cover 130 may be disposed on an upper part of the accommodation base 120 to enclose the culture chamber 110 in a cavity formed by the upper cover 130 and the accommodation chamber 121. The culture solution outlet 160 and the culture solution inlet 150 are connected with the culture solution channel 140. The culture solution inlet 150 may be used to perfuse a new culture solution into the culture solution channel 140, and the culture solution outlet 160 may be used to discharge the culture solution in the culture solution channel 140.

In some embodiments, the accommodation base 120 may be provided with the accommodation chamber 121, which may be used to accommodate the culture chamber 110. The culture chamber 110 may be accommodated in the accommodation chamber 121 and connected with a bottom wall of the accommodation chamber 121 or both the bottom wall of the accommodation chamber 121 and a side wall of the accommodation chamber 121. In some embodiments, the culture solution channel 140 may be formed between an outer side of the culture chamber 110 and an inner wall of the accommodation chamber 121. In some embodiments, there may be a certain gap between the culture chamber 110 and the accommodation chamber 121 such that the culture solution channel 140 is formed. As an example, in the embodiments shown in FIGS. 6 and 7, the culture chamber 110 is placed on the bottom wall of the accommodation chamber 121, and a chamber side wall 111 of the culture chamber 110 and the side wall of the accommodation chamber 121 are separated at a certain distance. The chamber side wall 111, the side wall of the accommodation chamber 121, and the bottom wall of the accommodation chamber 121 may jointly form the culture solution channel 140. In other embodiments, the accommodation chamber 121 may accommodate a plurality of culture chambers 110, which may be disposed in a certain rule. The adjacent two culture chambers 110 in the plurality of culture chambers 110 may be separated by a certain distance (e.g., chamber side walls 111 of the adjacent two culture chambers 110 are separated by a certain distance) or abut against each other (e.g., chamber side walls 111 of the adjacent two culture chambers 110 abut). When the chamber side walls 111 of the two adjacent culture chambers 110 are separated by a certain distance, the chamber side walls 111 of the adjacent culture chambers 110 and the bottom wall of the accommodation chamber 121 may also form the culture solution channel 140. The culture solution channel 140 may be perfused with culture solution. The culture solution may flow between the culture solution channel 140 and inside of the culture chamber 110 through a membrane material 114 disposed on the chamber side wall 111 of the culture chamber 110, so as to realize an exchange of the culture solution inside and outside the culture chamber 110 (i.e., the culture solution channel 140).

In some embodiments, the present disclosure does not specifically define a shape of the accommodation chamber 121, a size of the accommodation chamber 121, or the like. The shape and the size of the accommodation chamber 121 enable the culture chamber 110 to be partially accommodated therein and form a culture solution channel 140 with the culture chamber 110. In some embodiments, an internal contour shape of the accommodation chamber 121 may include a cuboid shape, a T-shape, a column shape, or the like. For example, in the embodiments shown in FIGS. 2 and 3, an internal contour shape of the accommodation chamber 121 is a T-shape. As another example, in the embodiments shown in FIGS. 6 and 7, an internal contour shape of the accommodation chamber 121 is a cuboid plate shape.

The culture chamber 110 refers to a chamber for accommodating a culture. During a culture process, the culture is located in the culture chamber 110, which grows and propagates by utilizing nutrients through the culture solution entering the culture chamber 110 through the culture solution channel 140.

In some embodiments, the culture chamber 110 may include the chamber side wall 111, a chamber bottom wall 112, and a chamber top wall 113. The chamber side wall 111 is enclosed on peripheral side of the chamber bottom wall 112 to form a chamber with a top opening, and the chamber bottom wall 112 is used as the bottom wall of the chamber. The chamber top wall 113 may be on the top of the chamber and may be opposite to the chamber bottom wall 112. In some embodiments, the chamber top wall 113 of the culture chamber 110 may not be necessary. As an example, in the embodiments shown in FIGS. 6 and 7, the culture chamber 110 may include the chamber bottom wall 112 and the chamber side wall 111 surrounding the chamber bottom wall 112, the chamber bottom wall 112 and the chamber side wall 111 jointly form the culture chamber 110 with the top opening and do not close the top of the culture chamber 110. In some embodiments, the chamber top wall 113 is connected and fixed with the chamber side wall 111 by means of a bonding connection, a riveting connection, a screw connection, an integrated molding, or the like.

In some embodiments, the chamber bottom wall 112 may be used to support the culture for attachment and growth. As an example, when the culture device 100 is applied to a two-dimensional culture mode, the culture is usually adherent cells, which need to attach to other objects to grow, and a surface of the chamber bottom wall 112 may be used for the adherent cells to attach to. As another example, when the culture device 100 is applied to a three-dimensional culture mode, the culture is usually wrapped with a matrix glue, which can be stably attached to the surface of the chamber bottom wall.

In some embodiments, in the two-dimensional culture mode or the three-dimensional culture mode, the culture is attached to the surface of the chamber bottom wall 112. Therefore, in the present disclosure, the surface of the chamber bottom wall 112 may also be called a culture surface, and observing the culture may be equivalent to observing the surface of the chamber bottom wall 112 for observation.

In some embodiments, the chamber bottom wall 112 may be composed of independent members. For example, the chamber bottom wall 112 may be a sheet-shaped member or a plate-shaped member made of biocompatible materials, the chamber bottom wall 112 may be connected with the chamber side wall 111 to form the culture chamber 110. The biocompatible materials may include but are not limited to, natural chitosan, sodium alginate, polyethylene glycol, bioceramics, or the like. In other embodiments, the chamber bottom wall 112 may be part of the bottom wall of the accommodation chamber 121. As an example, the chamber side wall 111 (for example, the membrane material 114) may be directly connected with the bottom wall of the accommodation chamber 121 to form a chamber having a top opening with the bottom wall of the accommodation chamber 121. The chamber is the culture chamber 110. The chamber bottom wall 112 of the culture chamber 110 is a part of the bottom wall of the accommodation chamber 121.

In some application scenarios, when it is needed to observe the culture in the culture chamber 110, a light source may be used to illuminate the bottom of the culture device 100 so that light may pass through the chamber bottom wall 112, and then the culture attached to the surface of the chamber bottom wall 112 may be observed through a lens.

Figure 3:
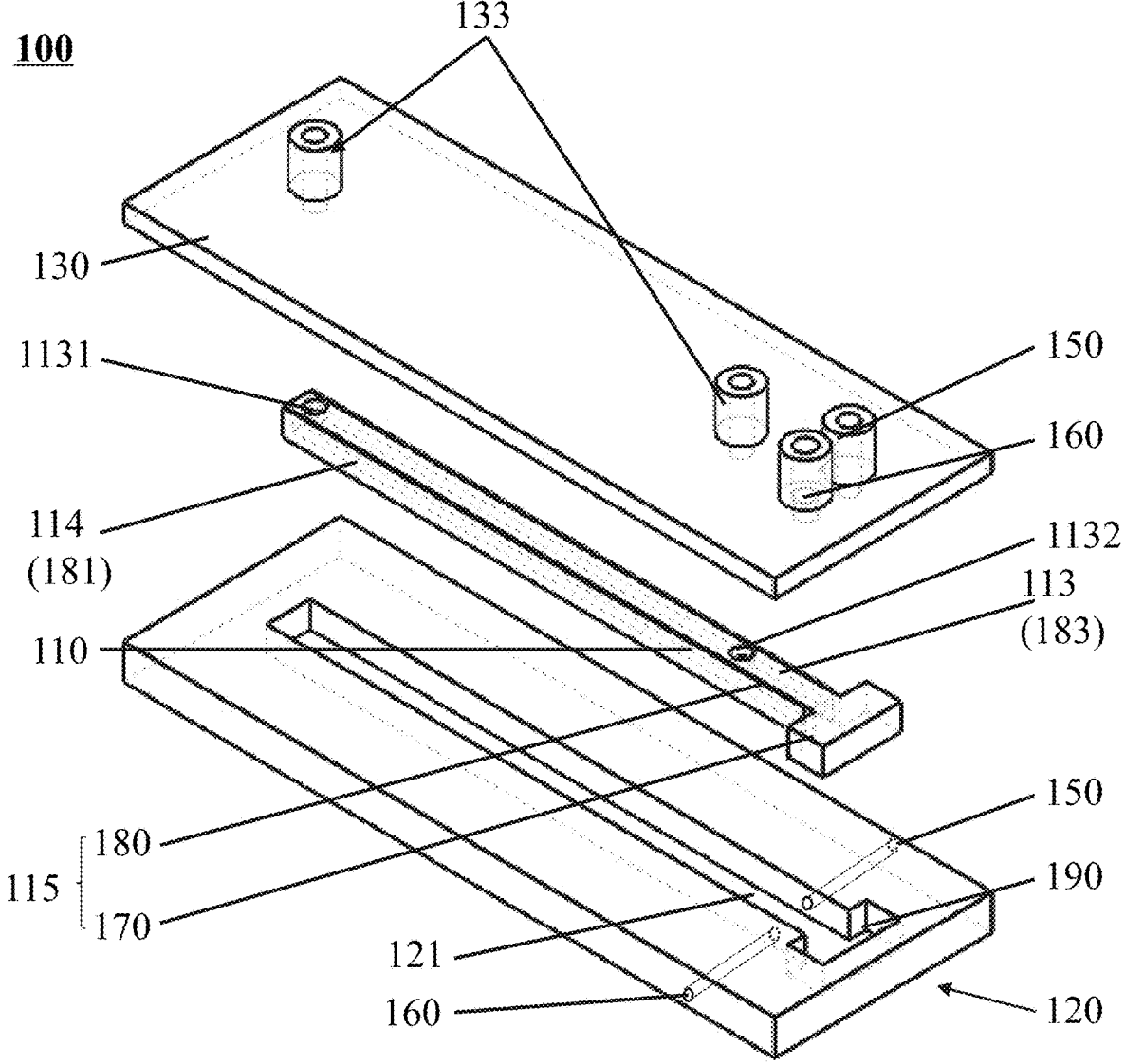
FIG. 3 is a schematic diagram illustrating an explosive view of an exemplary structure of a culture device including a membrane material according to some embodiments of the present disclosure.
Figure 8:
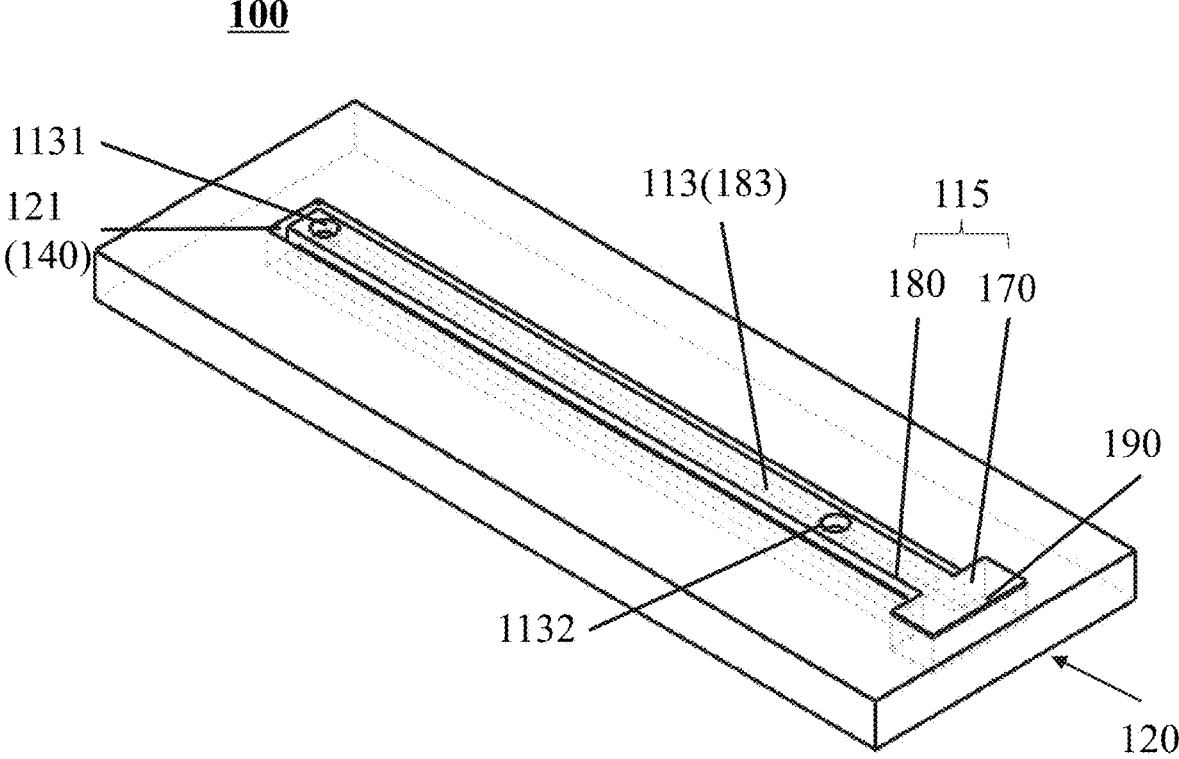
FIG. 8 is a schematic diagram illustrating an exemplary structure of the support frame matched with an accommodating component according to some embodiments of the present disclosure.

As shown in FIGS. 2, 3, and 8, in some embodiments, the culture chamber 110 may also include a culture outlet 1131 and a culture inlet 1132. The culture outlet 1131 and the culture inlet 1132 may be used to collect culture (i.e., take out the culture) from the culture chamber 110 and add culture (i.e., inoculate the culture) to the culture chamber 110, respectively. In some embodiments, when the culture chamber 110 does not include the chamber top wall 113, because of the top opening of the culture chamber 110, the culture may be inoculated and/or collected directly through the top opening. In some embodiments, when the culture chamber 110 includes the chamber top wall 113 (or a top plate 183), the culture outlet 1131 and the culture inlet 1132 may be disposed on the chamber top wall 113, and the culture may be inoculated and/or collected through the culture inlet 1132 and the culture outlet 1131 on the chamber top wall 113. As an example, in the embodiments shown in FIGS. 2 and 3, one end and another end of the chamber top wall 113 (i.e., top plate 183) are respectively provided with the culture inlet 1132 and the culture outlet 1131, which are used for culture inoculation and culture collection.

It should be noted that the present disclosure does not limit a count of the culture inlet 1132 and the culture outlet 1131. The count of the culture inlet 1132 and the culture outlet 1131 may be the same or different. In some embodiments, functions of the culture inlet 1132 and the culture outlet 1131 may be realized on a same structure. For example, only the culture inlet 1132 is opened, which may be used to add the culture to the culture chamber 110 or collect the culture. In some embodiments, the culture inlet 1132 and the culture outlet 1131 exist in the form of a through-hole structure in a specific shape, for example, a regular or irregular shape such as a circle, a square, a triangle, or a polygon.

In order to compare different groups of cultures at the same time, in some embodiments, a plurality of culture chambers 110 may be provided. In some embodiments, the plurality of culture chambers 110 may be accommodated in the accommodation chamber 121, and each culture chamber 110 may be used to cultivate different cultures for comparison. In some embodiments, an isolation component may be added in the culture chamber 110 to divide the culture chamber 110 into a plurality of culture sub-chambers to realize the function of simultaneous culturing a plurality of groups of cultures. As an example, the isolation component may be a sheet component, and the isolation component may be inserted at different positions of the culture chamber at intervals to divide the culture chamber into the plurality of culture sub-chambers. In some embodiments, the isolation component may be made of the membrane material 114 in the aforementioned embodiments. In some cases, the isolation component made of the membrane material may be used to segment the culture chamber 110, the isolation component may not only intercept the culture in each culture sub-chamber but also allow the culture solution to circulate between each culture sub-chamber.

Figure 4:
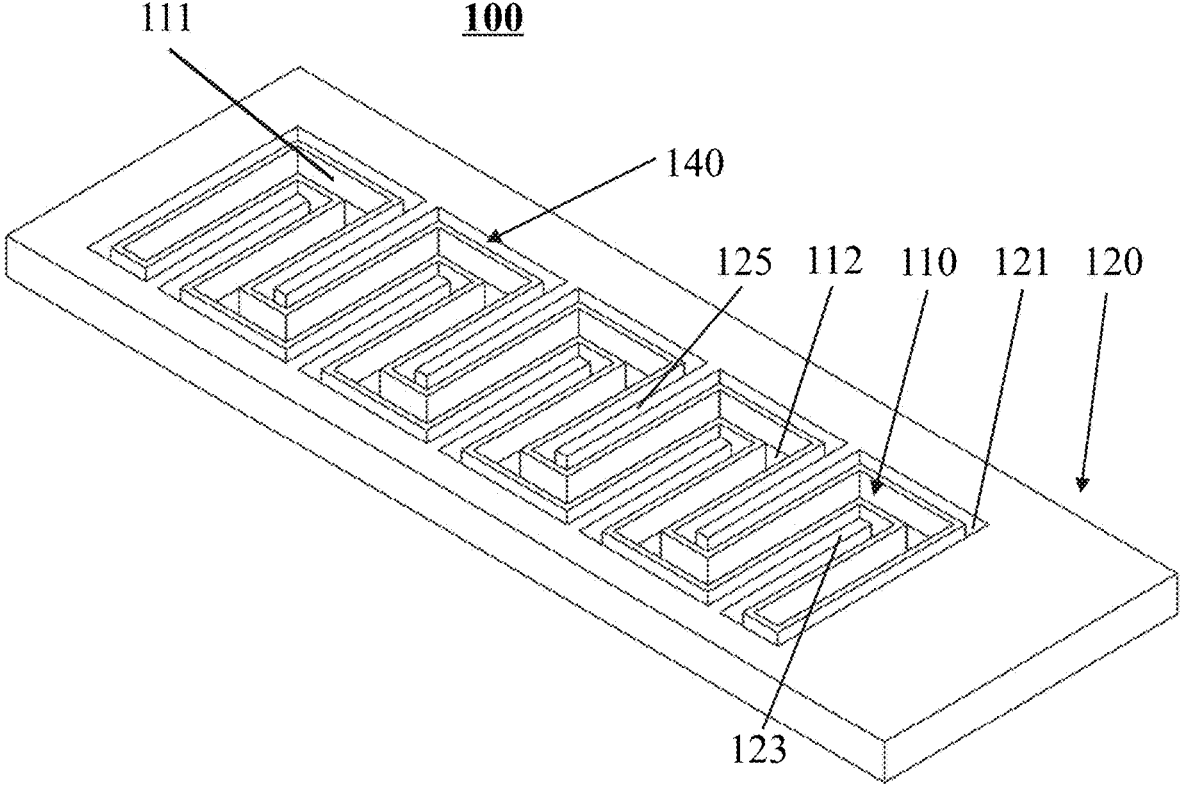
FIG. 4 is a schematic diagram illustrating an exemplary structure of a culture device according to other embodiments of the present disclosure.

FIG. 4 is a schematic diagram illustrating an exemplary structure of a culture device according to other embodiments of the present disclosure. As shown in FIG. 4, in some embodiments, the culture chamber 110 may include a plurality of bending U-shaped culture sub-chambers, and the two adjacent culture chambers are connected with each other. In some embodiments, the culture chamber 110 may be formed by the chamber side wall and a part of the bottom wall of the accommodation chamber. For example, the chamber side wall 111 may include a plurality of planar films connected in sequence, and two adjacent planar films may be perpendicular to each other. In some embodiments, the accommodation base 120 may include a first drainage component 123 and a second drainage component 125. The first drainage component 123 extends from the inner wall of the accommodation chamber 121 into a U-shaped notch formed by a U-shaped culture sub-chamber. The first drainage component 123 may guide the culture solution into the U-shaped notch formed by the U-shaped culture sub-chamber, which may increase a contact area between the culture solution channel 140 and the culture chamber 110 and improve an exchange rate of the culture solution. Similarly, a U-shaped notch is also formed between two adjacent U-shaped culture sub-chambers, and the second drainage component 125 extends into the U-shaped notch from the inner wall of the accommodation chamber 121 to guide the culture solution into the U-shaped notch, and improve the exchange rate of the culture solution.

Figure 5:
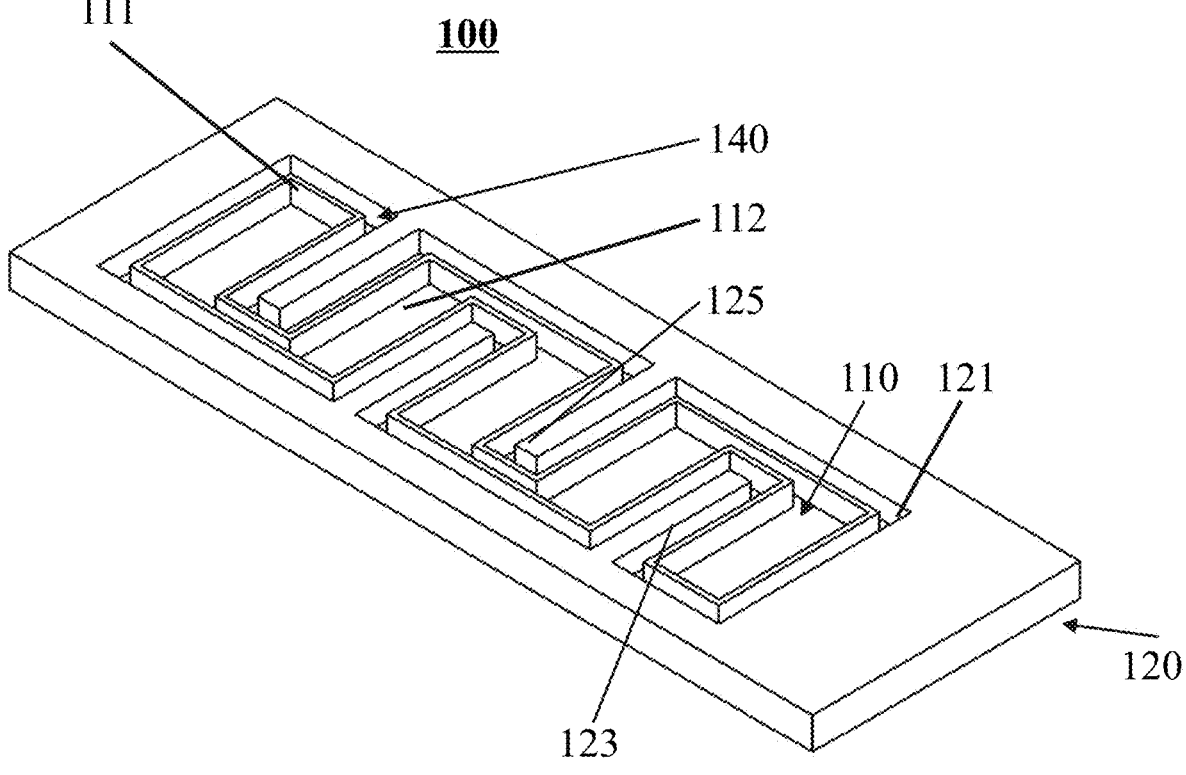
FIG. 5 is a schematic diagram illustrating an exemplary structure of a culture device according to yet other embodiments of the present disclosure.

FIG. 5 is a schematic diagram illustrating an exemplary structure of a culture device according to yet other embodiments of the present disclosure. Structures in FIG. 5 and FIG. 4 are the same or similar, but a difference is that the chamber bottom wall 112 of the U-shaped culture sub-chamber in FIG. 5 has a larger area, while a channel connecting two adjacent culture sub-chambers is narrower. Compared with a culture sub-chamber in FIG. 4, a culture sub-chamber in FIG. 5 may accommodate more cultures and cultures having a larger size (for example, a diameter of a culture).

Figure 6:
FIG. 6 is a schematic diagram illustrating an exemplary structure of a support frame according to some embodiments of the present disclosure.
Figure 6:
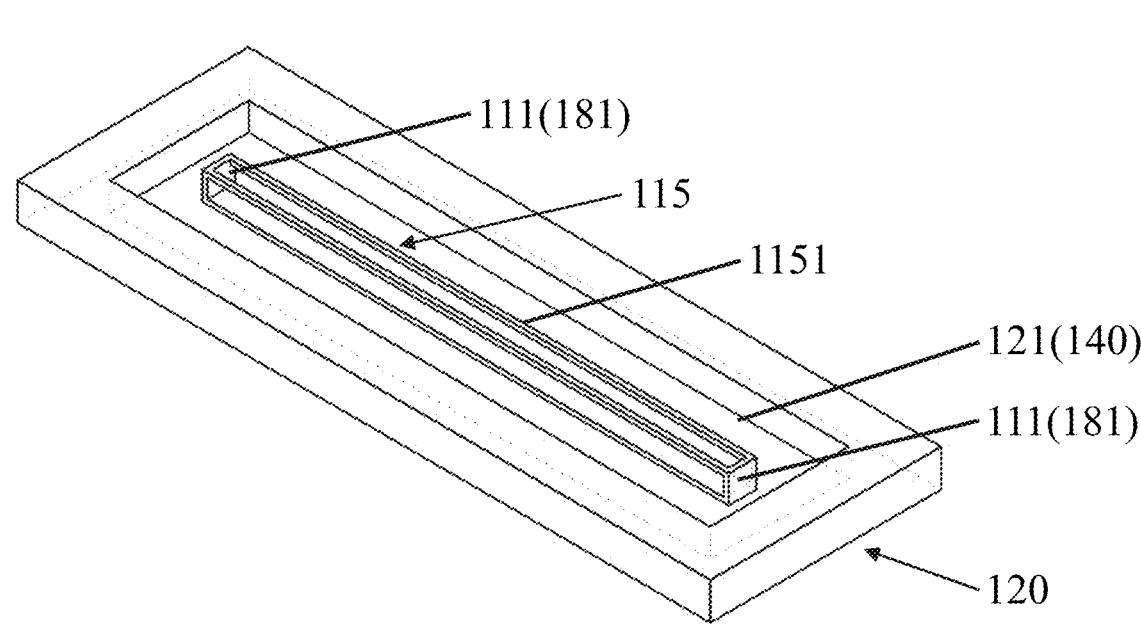
Figure 7:
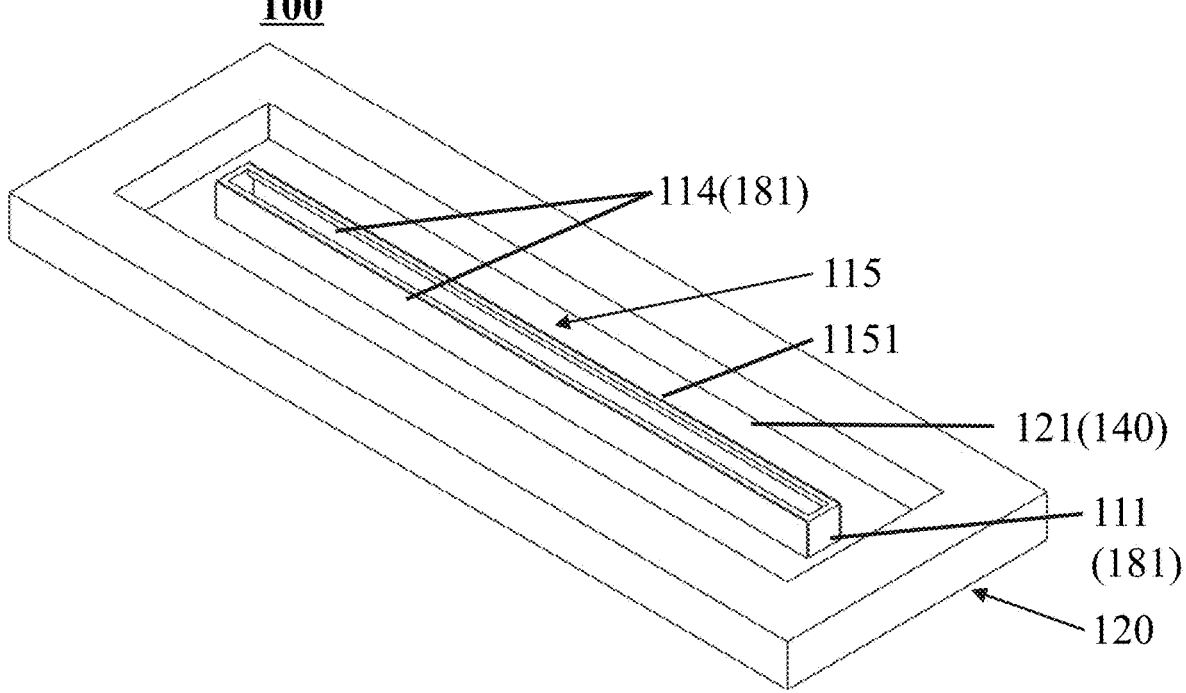
FIG. 7 is a schematic diagram illustrating an exemplary structure of a support frame provided with the membrane material according to some embodiments of the present disclosure.

FIG. 6 is a schematic diagram illustrating an exemplary structure of a support frame according to some embodiments of the present disclosure. FIG. 7 is a schematic diagram illustrating an exemplary structure of a support frame provided with the membrane material according to some embodiments of the present disclosure. As shown in FIG. 6, in some embodiments, the culture chamber 110 may also include a support frame 115 in addition to being formed by a direct connection (for example, a bonding connection, a rivet connection, an integrated molding, etc.) of the chamber side wall 111, the chamber bottom wall 112, and the chamber top wall 113. The support frame 115 may define an external contour of the culture chamber 110. In some embodiments, the external contour of the culture chamber 110 may be presented as a regular or irregular shape such as a cylinder shape, a cuboid shape, a polyhedron shape, or the like. The chamber bottom wall 112, the chamber side wall 111, and the chamber top wall 113 are fixed by the support frame 115 to form the culture chamber 110. In some cases, the support frame 115 is used to fix the chamber bottom wall 112, the chamber side wall 111, and the chamber top wall 113 of the culture chamber 110. The support frame 115 may improve the stability of the culture chamber 110.

The embodiments of the present disclosure do not limit the shape of the external contour of the support frame 115 and the shape of the external contour of the support frame 115 may be designed according to a shape of a required culture chamber 110. As shown in FIG. 6, in some embodiments, the support frame 115 has a cuboid shape. The support frame 115 may include four support columns 1151 that are parallel to each other. A first end of each support column 1151 is relatively fixed with a first end of other support columns 1151, and a second end of the support column 1151 is relatively fixed with a second end of other support columns 1151. For example, the support frame 115 may also include a connection column, which may fix a first end of two adjacent support columns 1151 and a second end of two adjacent support columns 1151, and finally form a cuboid-shaped support frame 115. In another example, the support frame 115 may fix the support columns 1151 through other structures. For example, in the embodiment shown in FIG. 6, both ends of the four support columns 1151 are respectively fixed by two side plates 181. In some embodiments, the chamber bottom wall 112 may be disposed between two adjacent support columns 1151. The chamber top wall 113 may be disposed between two adjacent support columns 1151 on a side opposite to the chamber bottom wall 112. The chamber side wall 111 (for example, the side plate 181) may be disposed between other adjacent support columns 1151 and an area enclosed by the connection columns at the first end and the second end of the support columns 1151. In some embodiments, a spacing distance between two adjacent support columns 1151 may be the same or different. For example, a spacing distance between two support columns 1151 for setting the chamber side wall 111 is the same. As another example, the spacing distance between the two support columns 1151 for setting the chamber side wall 111 may be less than a spacing distance between two support columns 1151 for setting the chamber bottom wall 112 and the chamber top wall 113.

In some embodiments, the chamber side wall 111, the chamber bottom wall 112, and the chamber top wall 113 may be fixed with the support columns 1151 and the connection columns through a physical connection method such as a bonding connection, a rivet connection, a screw connection, or the like. For the convenience of description, the membrane material 114 is taken as an example for description. For example, when fixing the membrane material 114, glue may be coated on surfaces of the support columns 1151, and then an edge of the membrane material 114 may be directly adhered to the support columns 1151 for fixation. In another example, a peripheral side of the membrane material 114 is provided with a fixing component (for example, a snap), and the support columns 1151 are provided with a structure adapted to the fixing component. The fixing component may be matched with the support columns 1151 to realize a fixing of the membrane material 114 and the support columns 1151, thereby fixing with the support frame 115. In some embodiments, the support frame 115 may be made of metal, plastic, or other materials.

In some embodiments, the support frame 115 may also include a hollow-out plate, which may be disposed between two adjacent support columns 1151 of the support frame 115. In some embodiments, the hollow-out plate is fixed with the support columns 1151 of the support frame 115 by means of a welding connection, a bonding connection, or the like. In some embodiments, the membrane material 114 may be attached to an inner or an outer surface of the hollow-out plate to be fixed with the support frame 115.

In some embodiments, when the support frame 115 is placed in the accommodation chamber 121, since the culture solution channel 140 needs to be formed between the culture chamber 110 and the accommodation chamber 121, there is a certain interval between the chamber side wall 111 of the culture chamber 110 and the side wall of the accommodation chamber 121. If the support frame 115 is placed in the accommodation chamber 121 without a fixing constraint, the support frame 115 may move on the bottom wall of the accommodation chamber 121, which may cause the culture chamber 110 to collide with the accommodation chamber 121. The culture chamber 110 may even be damaged, or the culture may overflow, and thus an observation of the culture by the staff member may be affected.

Based on the above reasons, in some embodiments, the support frame 115 in the culture chamber 110 may also include a limiting component 170. The accommodation chamber 121 may include a locking component 190 adapted to the limiting component 170. Through mutual cooperation of the limiting component 170 and the locking component 190, a position of the support frame 115 contained in the accommodation chamber 121 may be fixed to limit the movement of the support frame 115 on the bottom wall of the accommodation chamber 121.

In some embodiments, the locking component 170 may be a convex structure disposed on the support columns of the support frame 115. The convex structure may be disposed on the two support columns 1151 for fixing the chamber bottom wall 112, extend away from the support columns 1151 and form a certain angle with the support columns 1151. The locking component 190 may be a groove provided at the bottom of the accommodation chamber 121 that is adapted to the convex structure. When the culture chamber 110 is placed on the bottom wall of the accommodation chamber 121, the convex structure may be embedded in the groove at the bottom of the accommodation chamber 121, and the movement of the culture chamber 110 may be limited by a cooperation of the convex structure and the groove. In some embodiments, the convex structure may be a columnar member, a sheet member, or the like. A shape of the groove corresponds to the convex structure. In some embodiments, the convex structure may be fixed on the support columns of the support frame 115 by means of a welding connection, a bonding connection, a rivet connection, an integrated molding, or the like. In some embodiments, there is no limit to the count of convex structures. For example, the count of the convex structures may be 1, 2, or more, and the count of grooves matches the count of the convex structures.

FIG. 8 is a schematic diagram illustrating an exemplary structure of the support frame matched with an accommodating component according to some embodiments of the present disclosure. As shown in FIGS. 2, 3, and 8, in some embodiments, the support frame 115 may include a support body 180 and the limiting component 170 connected with the support body 180. The limiting component 170 is connected with one end of the support body 180. The accommodation base 120 includes the locking component 190 that may be matched with the limiting component 170, and the limiting component 170 may be matched with the locking component 190 to limit the movement of the support frame 115 on the bottom wall of the accommodation chamber 121. In this embodiment, the support body 180 is used to fix the chamber side wall 111 and the chamber bottom wall 112 to form the culture chamber 110. The limiting component 170 is used for cooperating with the locking component 190 to limit the movement of the support body 180. In some embodiments, the limiting component 170 may be a strip-shaped component, a block-shaped component, a ball-shaped component, or the like. Correspondingly, the locking component 190 may be a locking groove provided on the accommodation base 120 with an appropriate shape. The adaptation may mean that the shape and the size of the locking groove are the same as or similar to the shape and the size of the limiting component 170 (for example, the strip-shaped component), so that when the strip-shaped component is located in the locking groove, the strip-shaped component abuts against an inner wall of the locking groove and is prevented from moving. In some specific embodiments, the limiting component 170 is the strip-shaped component (which can be called a limiting strip), and the strip-shaped component may be connected with the support body 180 to form a "T"-shaped member, an "L"-shaped member, a cross-shaped member, an "H"-shaped member, or the like. For example, a count of the strip-shaped component is one, one end of the strip-shaped component is connected with one end of the support body 180 to form the "L"-shaped member. As another example, the middle of the strip-shaped component may be connected with one end of the support body 180 to form the "T"-shaped member. As another example, a count of strip-shaped components is two, and the middle of the two strip-shaped components are respectively connected with two ends of the support body 180 to form the "H"-shaped member.

In some embodiments, the limiting component 170 and the support body 180 may be disassembled with respect to each other. For example, the limiting component 170 is connected with one end of the support body 180 through a snap connection. In some embodiments, the limiting component 170 and the support body 180 may be fixedly connected, for example, the limiting component 170 and the support body 180 may be integrally formed.

Figure 9:
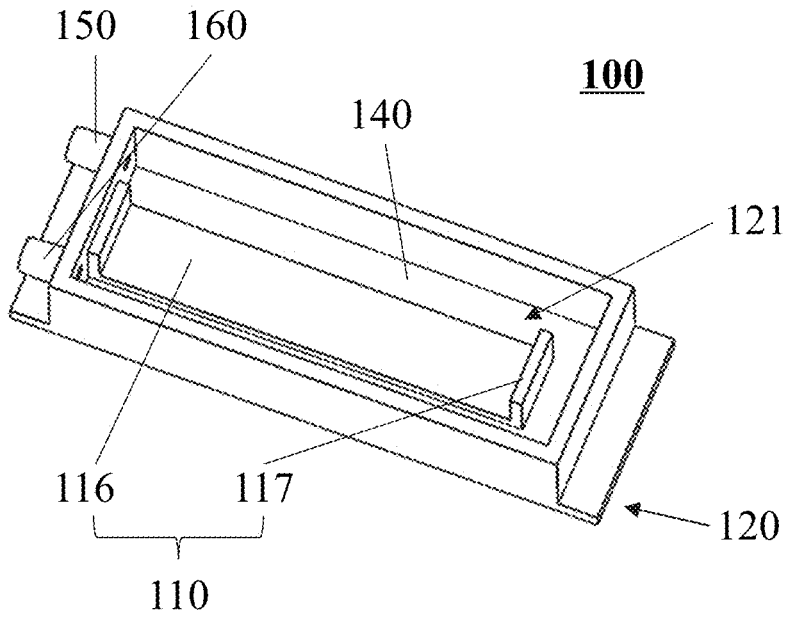
FIG. 9 is a structural diagram illustrating a connection of a bottom wall and a side wall of an accommodation chamber and a culture chamber according to some embodiments of the present disclosure.
Figure 10:
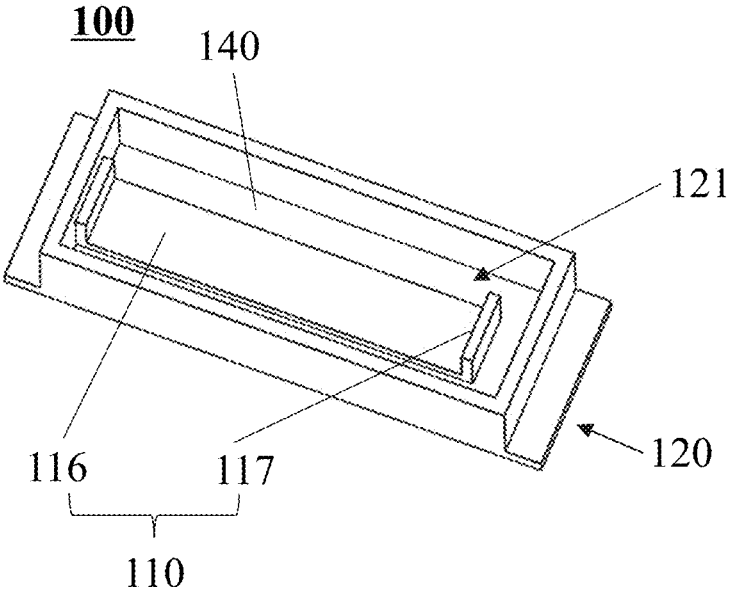
FIG. 10 is a schematic diagram illustrating an exemplary structure of a connection between the bottom wall and the side wall of the accommodation chamber and the culture chamber according to other embodiments of the present disclosure.

FIG. 9 is a structural diagram illustrating a connection of a bottom wall and a side wall of an accommodation chamber and a culture chamber according to some embodiments of the present disclosure. FIG. 10 is a schematic diagram illustrating an exemplary structure of a connection between the bottom wall and the side wall of the accommodation chamber and the culture chamber according to other embodiments of the present disclosure. In some embodiments, the limiting component 170 and the locking component 190 may not exist simultaneously. For example, a convex structure may be disposed on the inner wall of the accommodation chamber 121 to limit a movement of the culture chamber 110. The convex structure may be equivalent to a locking component 190 without the need to additionally dispose the limiting component 170. In some embodiments, the limiting component 170 and the locking component 190 may not be necessary, and the culture chamber 110 may be fixed with the accommodation chamber 121 by a physical connection. The physical connection mode may include a bonding connection, a rivet connection, a screw connection, an integrated molding, or the like. As shown in FIGS. 9 and 10, in some embodiments, the culture chamber 110 may include a chamber bottom plate 116 and two chamber side plates 117 disposed at both ends of the chamber bottom plate 116. The membrane material (such as the membrane material 114 in aforementioned embodiments) may be disposed on both sides of the chamber side plates 117 and the chamber bottom plate 116, and may be enclosed with the chamber bottom plate 116 and the chamber side plates 117 to form the culture chamber 110 with an opening. The chamber bottom plate 116 is connected with the bottom wall of the accommodation chamber 121, and the chamber bottom plate 116 may be used as the chamber bottom wall 112 of the culture chamber 110. The chamber side plates 117 and the membrane material 114 may be used as the chamber side wall 111 of the culture chamber 110. An outer wall of at least one of the two chamber side plates 117 is physically connected with the side wall of the accommodation chamber 121 to fix the culture chamber 110 and the accommodation chamber 121. Other chamber side plates 117 and the membrane material 114 that are not connected with the side wall of the accommodation chamber 121 are separated from the side wall of the accommodation chamber 121 by a certain distance to form the culture solution channel 140. As an example, as shown in FIG. 9, the chamber side plates 117 on a left side of the chamber bottom plate 116 are connected with the side wall of the accommodation chamber 121, and a U-shaped culture solution channel 140 is formed between two membrane materials 114, another chamber side plates 117, and the inner wall of the accommodation chamber 121. In some embodiments, the accommodation chamber 121 is provided with the culture solution inlet 150 and the culture solution outlet 160. The culture solution inlet 150 and the culture solution outlet 160 are respectively disposed on the side wall of the accommodation chamber 121 on both sides of the chamber side plates 117 (i.e., the chamber side plates 117 connected with the side wall of the accommodation chamber 121). In some cases, the culture solution may be perfused into the culture solution channel 140 through the culture solution inlet 150, and a part of the culture solution may be taken out from the culture solution channel 140 via the culture solution outlet 160 to realize the perfusion culture. The culture device shown in FIG. 10 is similar to the culture device shown in FIG. 9. A difference is that the accommodation chamber 121 in FIG. 10 is not provided with the culture solution inlet 150 and the culture solution outlet 160. Therefore, the culture device shown in FIG. 10 may be used in a stationary culture mode.

As shown in FIG. 2, in some embodiments, the support body 180 may include a top plate 183 and a bottom plate 182 with a certain distance, and one end of the top plate 183 and one end of the bottom plate 182 are fixedly connected with the limiting component 170. In some embodiments, the support body 180 may also include a side plate (e.g., the side plate 181 as shown in FIGS. 6 and 7, wherein the limiting component 170 is not shown in FIGS. 6 and 7) opposite to the limiting component 170. Another end of the top plate 183 and another end of the bottom plate 182 are connected with the side plate 181. In some embodiments, a plurality of chamber side walls 111 between the top plate 183 and the bottom plate 182 in the support body 180 may include the membrane material 114. As an example, as shown in FIG. 7, when the support body 180 is provided with a side plate 181, the chamber side wall 111 may include the side plate 181 and the membrane material 114, and the membrane material 114 may be disposed between two adjacent support columns 1151 between the top plate 183 and the bottom plate 182. As another example, when the side plate 181 is not disposed on the support body 180, the chamber side wall 111 may all be composed of the membrane material 114, that is, the side plate 181 in the aforementioned example is replaced by the membrane material 114. In some cases, the culture solution may be exchanged by entering and exiting the culture chamber 110 through the chamber side wall 111 (e.g., the membrane material 114) adjacent to the limiting component 170. In some embodiments, in order to improve an exchange rate of the culture solution, the chamber side wall 111 opposite to the limiting component 170 on the support body 180 may also be composed of the membrane material 114, that is, the chamber side wall 111 between the connection columns at the first end (the second end of the support columns 1151 is connected with the limiting component 170) of the support columns 1151 is also composed of the membrane material 114. In some cases, the chamber side wall 111 on the support body 180 is composed of the membrane material 114, which is equivalent to increasing a contact area between the culture chamber 110 and the culture solution channel 140, thus improving the exchange rate of the culture solution. In some embodiments, the top plate 183 on the support body 180 may not be necessary. For example, the support body 180 may only include the bottom plate 182, the side plate 181, and the membrane material 114, wherein the bottom plate 182, the side plate 181, and the membrane material 114 may enclose the culture chamber 110 with an opening. As another example, the support body may only include the bottom plate 182 and the membrane material 114, wherein the bottom plate 182 and the membrane material 114 may enclose the culture chamber 110 with an opening.

As shown in FIGS. 7 and 8, in some embodiments, an outer side of the chamber side wall 111 disposed on the support body 180 is separated from the inner side wall of the accommodation chamber 121 at a preset distance so that the culture solution channel 140 is a U-shaped channel surrounding the culture chamber 110. Since the gap between the limiting component 170 (i.e., the limiting strip) and the locking component 190 (i.e., the locking groove) is small, it can be considered that the culture solution does not flow between the locking groove and the limiting strip. Two ends of a U-shaped culture solution channel 140 are respectively located on two sides of a connection between the limiting component 170 and the support body 180. In this embodiment, by setting the culture solution channel 140 as the U shape and surrounding the culture chamber 110, each chamber side wall 111 on the support body 180 except for the chamber side wall 111 connecting with the limiting component 170 may be in direct contact with the culture solution channel 140. The contact area between the culture chamber 110 and the culture solution channel 140 is increased, and the exchange rate of the culture solution is improved.

In some embodiments, a preset distance between the outer side of the chamber side wall 111 on the support body 180 and the inner side wall of the accommodation chamber 121 may be within a range of 1 mm to 30 mm. In some embodiments, the preset distance between the outer side of the chamber side wall 111 on the support body 180 and the inner side wall of the accommodation chamber 121 may be within a range of 1.5 mm to 20 mm. In some embodiments, the preset distance between the outer side of the chamber side wall 111 on the support body 180 and the inner side wall of the accommodation chamber 121 may be within a range of 2 mm to 10 mm. In some embodiments, a ratio of a width of the support body 180 to a width of the accommodation chamber 121 may be within a range of 0.1-0.9. In some embodiments, a ratio of the width of the support body 180 to the width of the accommodation chamber 121 may be within a range of 0.2-0.8. In some embodiments, a ratio of the width of the support body 180 to the width of the accommodation chamber 121 may be within a range of 0.25 to 0.75. A width of the support body 180 refers to a distance between two chamber side walls 111 disposed on the two adjacent support columns 1151. A width of the accommodation chamber 121 refers to a size of the inner side wall of the accommodating chamber 121 along a width direction of the support body 180.

In some embodiments, the culture solution inlet 150 and the culture solution outlet 160 may be connected with two ends of the U-shaped culture solution channel 140, respectively. In this embodiment, by connecting the culture solution outlet 160 and the culture solution inlet 150 with two ends of the U-shaped culture solution channel 140, respectively, the culture solution may pass through all the chamber side walls 111 in contact with the culture solution channel 140, and the exchange rate of the culture solution is effectively improved. In some embodiments, the culture solution outlet 160 and the culture solution inlet 150 may perfuse a new culture solution into the culture solution channel 140 or take out part of the culture solution from the culture solution channel 140 through a top opening of the culture solution channel 140. As shown in FIGS. 2 and 3, in other embodiments, the culture solution outlet 160 and the culture solution inlet 150 may be disposed on the side wall of the accommodation chamber 121 to connect the culture solution channel 140 with the outside.

In some application scenarios, the culture solution inlet 150 and the culture solution outlet 160 may be used to perfuse and remove the culture solution in a perfusion culture mode or a non-perfusion culture mode (e.g., a stationary culture mode). In some embodiments, when the culture device 100 is used in the perfusion culture mode, the culture solution may enter or exit the culture solution channel through the culture solution inlet 150 and the culture solution outlet 160 at a specific rate.

In some embodiments, the culture solution inlet 150 and the culture solution outlet 160 may not be necessary. As shown in FIG. 10, when the culture device 100 is applied to the stationary culture mode, the culture solution in the culture solution channel 140 does not need to be replaced, so the culture solution does not need to be perfused and taken out through the culture solution inlet 150 and the culture solution outlet 160.

In some embodiments, the upper cover 130 may include a culture inoculation port 133, the culture solution inlet 150, and the culture solution outlet 160. The culture solution outlet 160 is used for discharging the culture solution, and the culture solution inlet 150 is used for injecting the culture solution. It is worth noting that functions of the culture solution inlet 150 and the culture solution outlet 160 may be replaced with each other. For example, the culture solution outlet 160 is used to inject the culture solution, and the culture solution inlet 150 is used to discharge the culture solution. The upper cover 130 may be above the culture chamber 110 and close to the accommodation chamber 121. In some embodiments, the culture inoculation port 133 may be connected with the culture inlet 1132 and the culture outlet 1131 (e.g., the culture inlet 1132 and the culture outlet 1131 disposed on the chamber top wall 113 (i.e., the top plate 183)), and the culture inlet 150 and the culture outlet 160 may be connected with the culture solution channel 140. At this time, the culture may be inoculated or collected through the culture inoculation port 133 disposed on the upper cover 130, and the new culture solution may be perfused into the culture solution channel 140 through the culture solution inlet 150 and the culture solution outlet 160, or part of the culture solution may be taken out of the culture solution channel 140.

In some embodiments, the culture inoculation port 133, the culture solution inlet 150, and the culture solution outlet 160 may be a through-hole structure of a certain shape, for example, a regular or irregular shape such as a circle, a square, or the like. In some embodiments, a tube body may be disposed at a port of the above-mentioned through hole. The tube body may be connected with an external conveying device and an external collecting device for inoculation of the culture, as well as the injection and collection of the culture solution.

In some embodiments, the culture device 100 provided in the present disclosure may be applied to a culture mode including the perfusion culture and the non-perfusion culture (for example, the stationary culture). Using the culture device 100 for above-mentioned culture process may effectively improve the culture efficiency and meet demand for culture products.

A process of the stationary culture includes: inoculating the culture into the culture chamber 110 through the culture inoculation port 133 or the culture inlet 1132 and making the culture adhere to the chamber bottom wall 112. Cultures include organs, cells or cell clusters, or the like. The culture fluid is perfused into the culture solution channel 140 through the culture solution inlet 150 or the opening (e.g., in the embodiment shown in FIG. 6, the culture device 100 may not be provided with the upper cover 130, so an upper part of the culture solution channel 140 is open) of the culture solution channel 140. The culture device 100 is then left to stand. The culture solution in the culture solution channel 140 may enter and exit the culture chamber 110 through the membrane material 114 on the chamber side wall 111, and exchange with the culture solution in the culture chamber 110. The culture in the culture chamber 110 absorbs nutrients in the culture solution for growth and reproduction. Finally, a cultured culture is taken out through the culture inoculation port 133 or the culture outlet 1131.

A process of perfusion culture includes: inoculating the culture into the culture chamber 110 through the culture inoculation port 133 or the culture inlet 1132 and attaching the culture to the chamber bottom wall 112. The culture includes organs, cells, cell clusters, or the like. The culture solution is perfused into the culture solution channel 140 through the culture solution inlet 150 or the opening of the culture solution channel 140. During the culturing process, the new nutrient solution is perfused into the culture solution channel 140 continuously or intermittently through the culture solution inlet 150 and the culture solution outlet 160 respectively, and the part of the culture solution is taken out from the culture solution channel 140, respectively, so the culture in the culture solution channel 140 is updated. The culture solution in the culture solution channel 140 may enter and exit the culture chamber 110 through the membrane material 114 on the chamber side wall 111, and exchange with the culture solution in the culture chamber 110. The culture in the culture chamber 110 absorbs the nutrients in the culture solution for growth and reproduction. Finally, a cultured culture is taken out through the culture inoculation port 133 or the culture outlet 1131.

Figure 11:
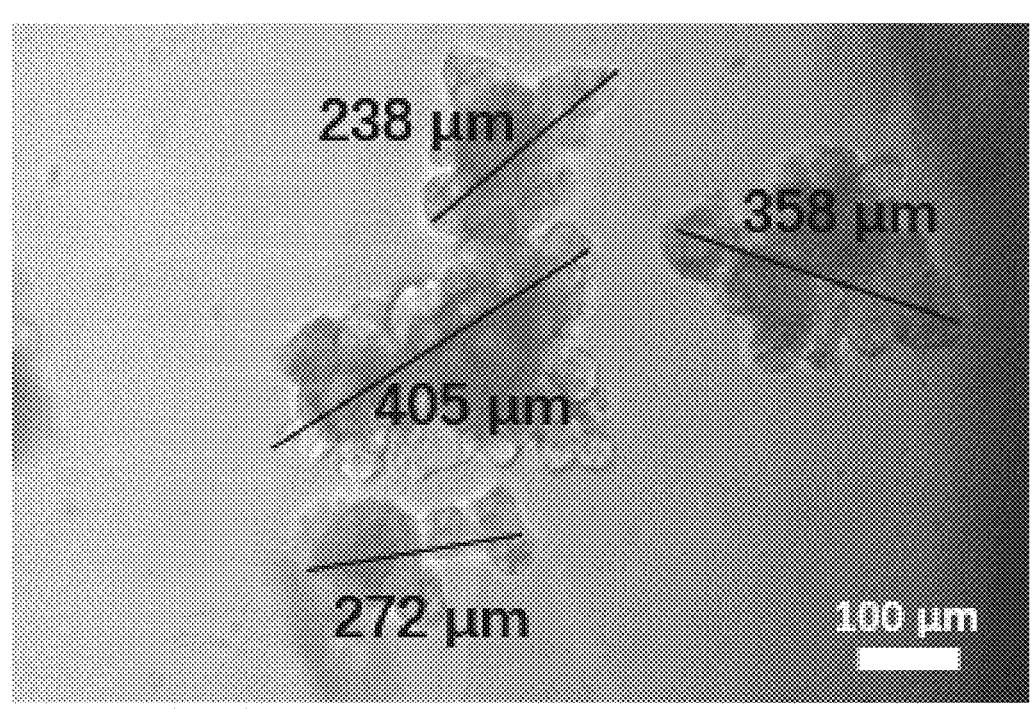
FIG. 11 is a schematic diagram illustrating a size of a culture obtained from the intestinal organ in the culture device 100 provided in the present disclosure according to some embodiments of the present disclosure.
Figure 12:
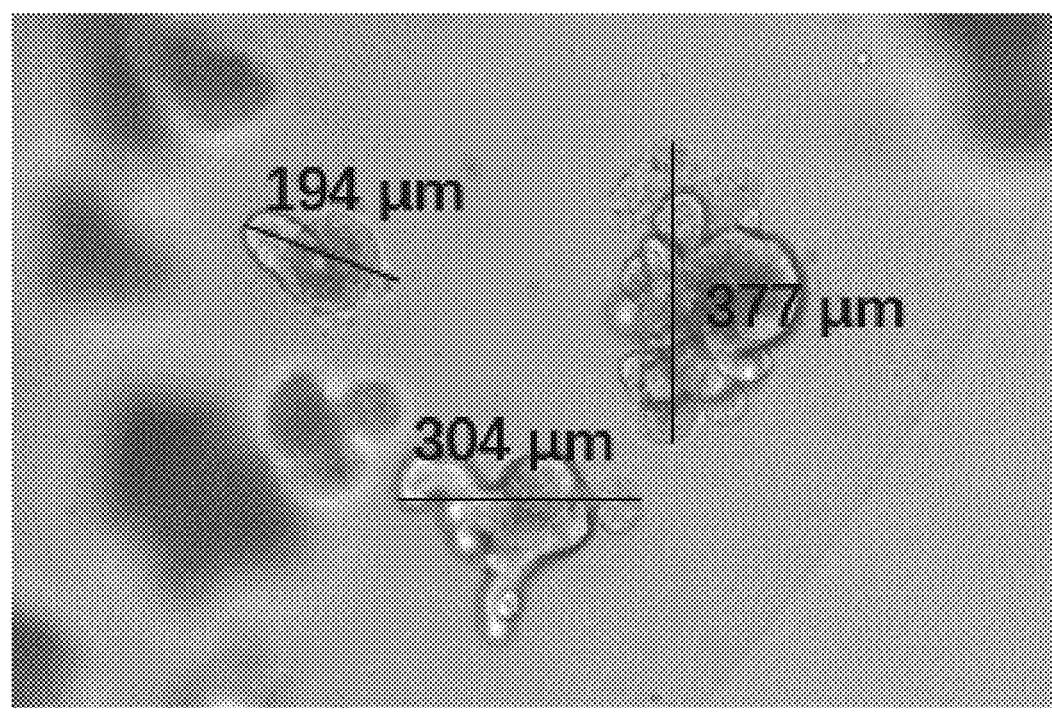
FIG. 12 is a schematic diagram illustrating a size of an intestinal organ of the control group 1 according to some embodiments of the present disclosure.
Figure 13:
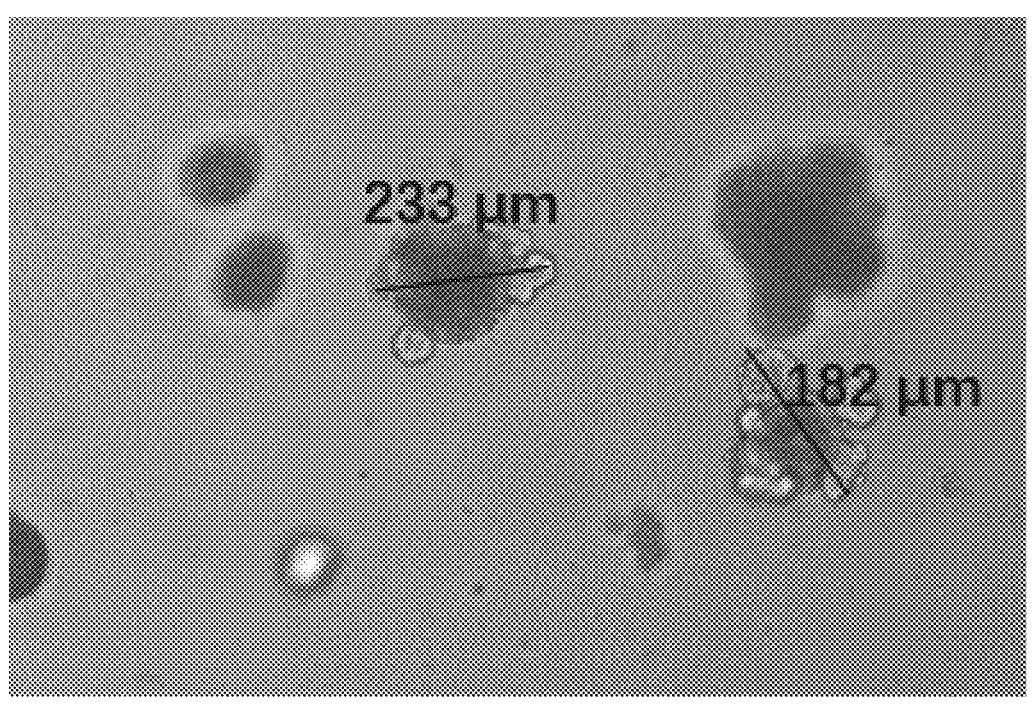
FIG. 13 is a schematic diagram illustrating a size of an intestinal organ of the control group 2 according to some embodiments of the present disclosure.
Figure 14:
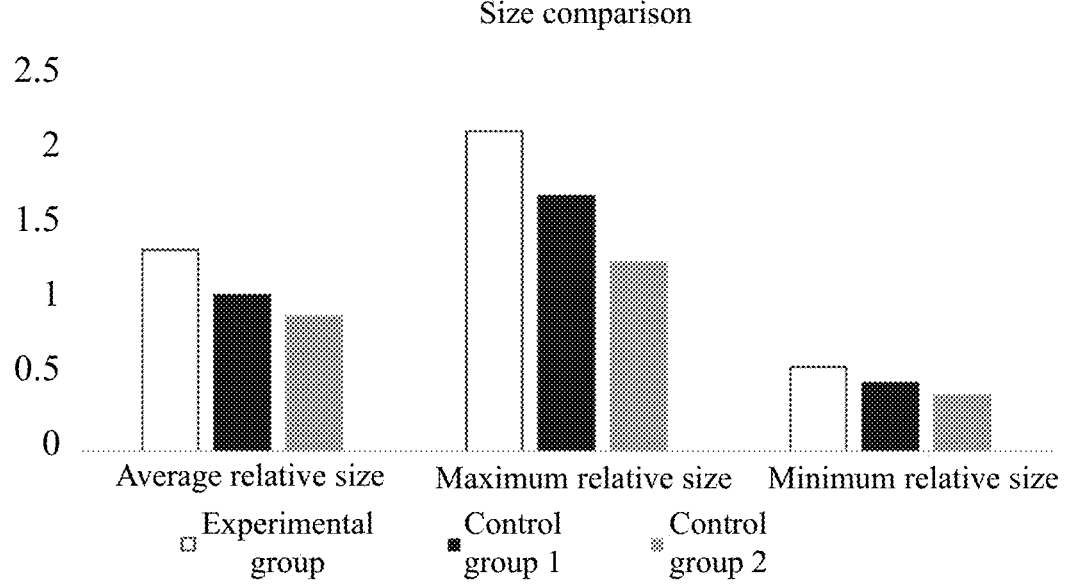
FIG. 14 is a schematic diagram illustrating a comparison of the size of the cultured intestinal organs according to some embodiments of the present disclosure.
Figure 15:
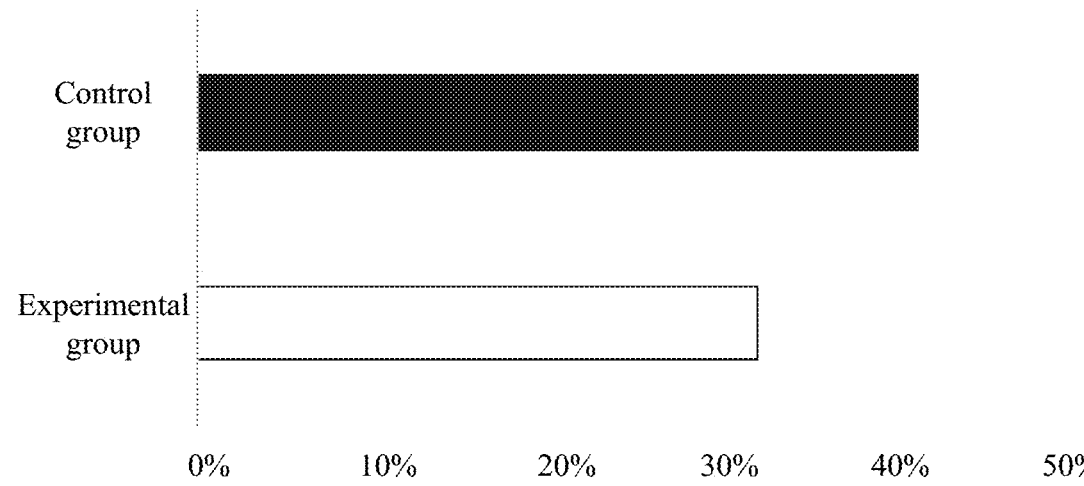
FIG. 15 is a schematic diagram illustrating a deviation of the size of the cultured intestinal organs according to some embodiments of the present disclosure.
Figure 16:
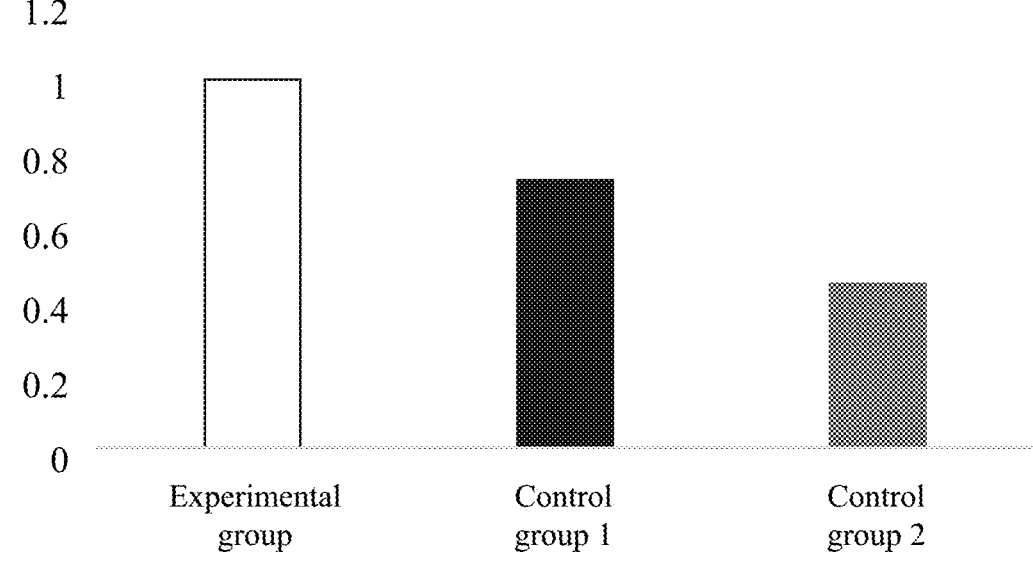
FIG. 16 is a schematic diagram illustrating a relative vitality of the cultured intestinal organs according to some embodiments of the present disclosure.

FIG. 11 is a schematic diagram illustrating a size of a culture obtained from the intestinal organ in the culture device 100 provided in the present disclosure according to some embodiments of the present disclosure. FIG. 12 is a schematic diagram illustrating a size of an intestinal organ of the control group 1 according to some embodiments of the present disclosure. FIG. 13 is a schematic diagram illustrating a size of an intestinal organ of the control group 2 according to some embodiments of the present disclosure. FIG. 14 is a schematic diagram illustrating a comparison of the size of the cultured intestinal organs according to some embodiments of the present disclosure. FIG. 15 is a schematic diagram illustrating a deviation of the size of the cultured intestinal organs according to some embodiments of the present disclosure. FIG. 16 is a schematic diagram illustrating a relative vitality of the cultured intestinal organs according to some embodiments of the present disclosure.

In some embodiments, using the culture device 100 in the present disclosure for culture may effectively improve culture efficiency, and the quality of a culture obtained may also be improved. The culture quality may include a vitality of the culture, an average size of the culture, a maximum size of the culture, a minimum size, and a size deviation. The culture efficiency may include the culture efficiency in unit volume, relative culture efficiency in unit volume, or the like. For the convenience of description, an intestinal organoid is taken as an example of the culture for illustration. The intestinal organ is cultured by the perfusion culture as described in the aforementioned embodiments through the culture device 100 provided in the present disclosure and a culture device for control, respectively. The culture device used for control may be Thermofisher 144530 24 well plate. FIG. 11 shows a size of a culture obtained from the intestinal organ in the culture device 100 provided in the present disclosure. FIGS. 12 and 13 respectively show the size of the culture obtained from the intestinal organ in the culture device for control. The culture used in FIG. 12 is an intestinal organ wrapped in a small glue droplet, while the culture used in FIG. 13 is an intestinal organ wrapped in a large glue droplet. It may be seen from FIGS. 11-13 that size uniformity of a culture obtained by using the culture device 100 in the present disclosure is better. The size uniformity refers to an average deviation between sizes of a plurality of cultures. FIG. 14 shows an average relative size, a maximum relative size, and a minimum relative size of a culture obtained under the three culture modes. FIG. 15 shows a size deviation of cultures cultivated by using the culture device 100 and the culture device used for the control. The size deviation may reflect a level of uniformity. The larger the size deviation, the worse the uniformity, and the smaller the size deviation, the better the uniformity. It can be seen from FIGS. 14 and 15 that a size of the culture cultured by the culture device 100 provided in the present disclosure is larger and the uniformity is better. In addition, FIG. 16 shows a vitality of a culture obtained in the three culture modes. It can be seen from FIG. 16 that the vitality of the culture obtained by using the culture device 100 provided in the present disclosure is better. Using the culture device 100 provided in the present disclosure for culture, a volume of consumables is smaller, an effective cultivation volume is larger, a relative operation efficiency is higher, a reference rate is larger, a volume utilization rate is higher, and the cultured culture has stronger vitality, larger size, and higher cultivation efficiency.

Possible beneficial effects of the culture device of the embodiments in the present disclosure include, but are not limited to: (1) by setting the membrane material on the chamber side wall to increase the angle between the plane where the membrane material is located and the chamber bottom wall, a shadow area of the membrane material in a microscope field of view under illumination of a light source is reduced, and interference of the membrane material to the staff member regarding observation of the culture under the microscope is reduced; (2) through a cooperation of the culture chamber and the accommodation chamber, a culture solution channel surrounding the culture chamber is formed outside the chamber side wall of the culture chamber, which increases a contact area between the culture solution channel and the culture chamber, and improves the exchange rate of the culture solution; (3) the outer contour of the culture chamber is defined by the support frame and the side wall, the bottom wall and the top wall of the chamber are fixed by the support frame, which can improve stability of the culture chamber; (4) by setting a limiting component on the support frame and a locking component on the accommodation component, a cooperation of the limiting component and the locking component is used to limit a movement of the culture chamber on the bottom wall of the accommodation chamber during a culture process, so as to improve the stability of the culture chamber. The above is only a preferred embodiment of the present disclosure, and does not limit the present disclosure. Any modification, equivalent replacement, and improvement made within the spirit and principles of the present disclosure should be included in the scope of protection of the present disclosure.

What is claimed is:

1. A culture device, comprising:
   an accommodation base, wherein an accommodation chamber is disposed on the accommodation base and includes a culture chamber for accommodating a culture, wherein
   the culture chamber includes one or more U-shaped culture sub-chambers, a chamber bottom wall and a chamber side wall surrounding the chamber bottom wall; wherein
   a culture solution channel is formed between an outer side of the chamber side wall and an inner wall of the accommodation chamber;
   the culture solution channel includes a U-shaped channel surrounding the one or more U-shaped sub-chambers; and
   at least a part of the chamber side wall includes a membrane material, a plane where the membrane material is located intersecting with the chamber bottom wall.

2. The culture device of claim 1, wherein a projected area on the chamber bottom wall projected by the membrane material in a direction perpendicular to the chamber bottom wall does not exceed 50% of an area of the chamber bottom wall.

3. The culture device of claim 1, wherein the culture chamber further includes a support frame defining an external contour of the culture chamber, the chamber bottom wall and the chamber side wall being fixed relative to the support frame.

4. The culture device of claim 1, wherein the chamber side wall includes a hollow-out plate and the membrane material is attached to the hollow-out plate.

5. The culture device of claim 3, wherein the membrane material is fixed on the support frame by a physical connection.

6. The culture device of claim 3, wherein the support frame includes four support columns, wherein an end of each of the four support columns is fixed relative to an end of another one of the four support columns.

7. The culture device of claim 1, wherein the accommodation base includes a first drainage component extending from the inner wall of the accommodation chamber into a U-shaped notch formed by one of the one or more U-shaped culture sub-chambers.

8. The culture device of claim 1, wherein:

the one or more U-shaped culture sub-chambers include at least two culture sub-chambers, and the accommodation base includes a second drainage component extending from the inner wall of the accommodation chamber into a U-shaped notch formed by two adjacent U-shaped culture sub-chambers of the at least two culture sub-chambers.

9. The culture device of claim 1, wherein one or more isolation components are disposed in the culture chamber to separate the culture chamber into two or more culture sub-chambers, at least a part of the one or more isolation components including the membrane material.

10. The culture device of claim 3, wherein the accommodation base includes a locking component configured to limit a movement of the support frame on a bottom wall of the accommodation chamber.

11. The culture device of claim 10, wherein the support frame includes a support body and a limiting component, the limiting component being connected with one end of the support body, wherein:

the locking component is matched with the limiting component, and a matching of the locking component and the limiting component limits the movement of the support frame on the bottom wall of the accommodation chamber.

12. The culture device of claim 11, wherein:

the limiting component and the support body form a member with a T-shape, an L-shape, an H-shape, or a cross shape, and the accommodation chamber on the accommodation base is a groove matched with the member.

13. The culture device of claim 11, wherein the support body includes a bottom plate, one end of the bottom plate being fixedly connected with the limiting component.

14. The culture device of claim 13, wherein the support body further includes a top plate, wherein there is a certain distance between the bottom plate and the top plate, and one end of the top plate is fixedly connected with the limiting component.

15. The culture device of claim 14, wherein the support body further includes a side plate opposite to the limiting component, another end of the top plate and another end of the bottom plate being connected with the side plate.

16. The culture device of claim 14, wherein one or more chamber side walls between the top plate and the bottom plate of the support body include the membrane material.

17. The culture device of claim 11, wherein a ratio of a width of the support body to a width of the accommodation chamber is within a range of 0.1-0.9.

18. The culture device of claim 14, wherein one end and another end of the top plate are respectively provided with a culture outlet and a culture inlet.

19. The culture device of claim 18, wherein the culture device further includes an upper cover, wherein the upper cover is provided with a culture inoculation port, a culture solution inlet, and a culture solution outlet, wherein the culture inoculation port corresponds to the culture outlet and the culture inlet; and the culture solution inlet and the culture solution outlet communicate with the culture solution channel.

* * * * *